United States Patent [19]

Faulkner

[11] Patent Number: 5,005,432
[45] Date of Patent: Apr. 9, 1991

[54] SAMPLING VALVE

[76] Inventor: Douglas L. Faulkner, 281 Gerry Ct., Walnut Creek, Calif. 94596

[21] Appl. No.: 510,600

[22] Filed: Apr. 18, 1990

Related U.S. Application Data

[63] Continuation-in-part of Ser. No. 312,471, Feb. 21, 1989, abandoned.

[51] Int. Cl.⁵ ............................................. G01N 1/00
[52] U.S. Cl. ..................................................... 73/863.86
[58] Field of Search ............ 73/863.41, 863.71–863.73, 73/863.81, 863.82, 863.85, 863.86, 863.52, 863.61, 863.83, 864.86, 864.33, 864.34, 864.51

[56] References Cited

U.S. PATENT DOCUMENTS

| 2,350,323 | 6/1944 | Cochran et al. | 83/863.61 |
| 3,683,700 | 8/1972 | Wilfong | 73/863.86 |
| 3,744,319 | 7/1973 | Harmes | 73/863.86 |
| 4,174,632 | 11/1979 | Jansen | 73/863.86 |
| 4,456,014 | 6/1984 | Buck et al. | 73/863.86 |
| 4,549,440 | 10/1985 | Fournier et al. | 73/863.86 |
| 4,688,436 | 8/1987 | Richon et al. | 83/863.71 |
| 4,800,761 | 1/1989 | Spencer | 73/863.71 |

FOREIGN PATENT DOCUMENTS

| 2752284 | 6/1978 | Fed. Rep. of Germany | 73/863.86 |
| 133345 | 7/1985 | Japan | 73/863.71 |
| 200795 | 8/1967 | U.S.S.R. | 73/863.86 |
| 549706 | 3/1977 | U.S.S.R. | 73/863.86 |

Primary Examiner—Robert Raevis
Attorney, Agent, or Firm—George W. Wasson

[57] ABSTRACT

A sampling valve assembly for use in sampling fluid streams under hazardous conditions. The assembly is adapted to be attached to a conduit of a process stream to cause a sample of the stream to pass through the assembly. The assembly includes a restricted axial passageway and gallery area for controlling the sample stream to provide a clean, representative sample at manageable conditions of pressure, velocity and turbulence where the sample of the sample stream may be taken. The sample exit port includes a conduit intended for eliminating dripping of sample material from the conduit.

12 Claims, 2 Drawing Sheets

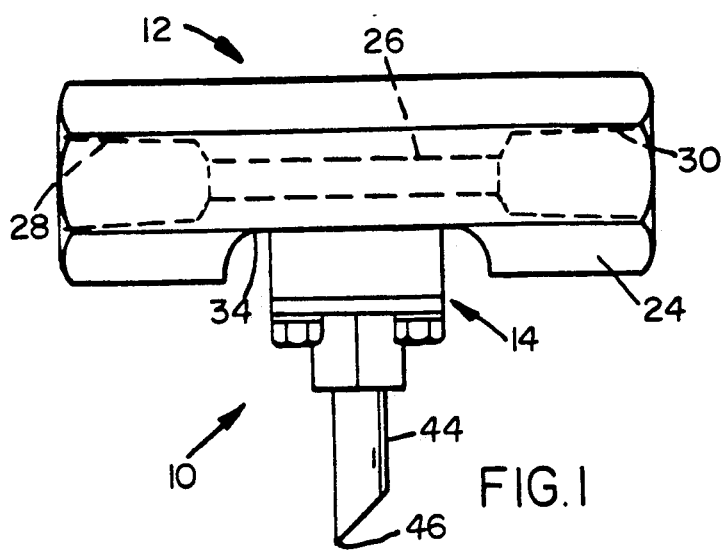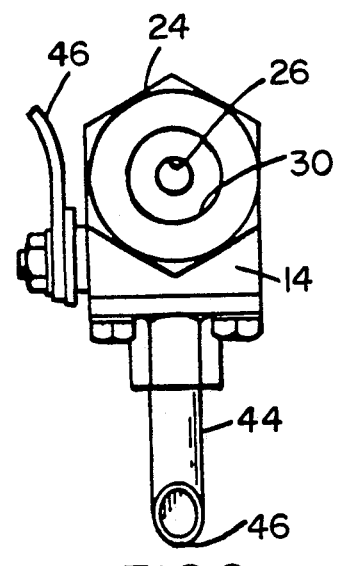
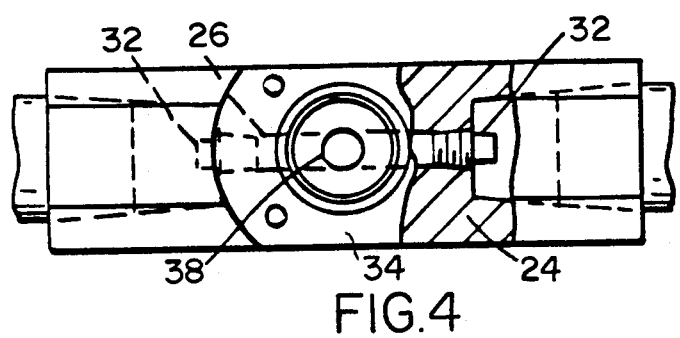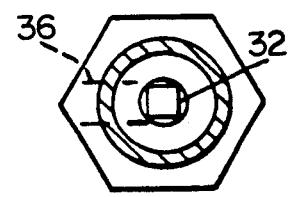
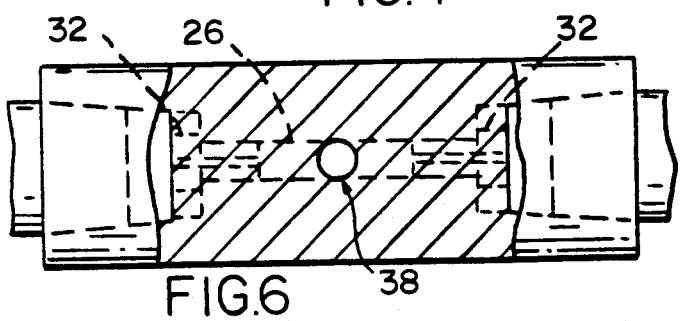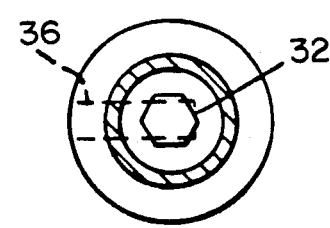
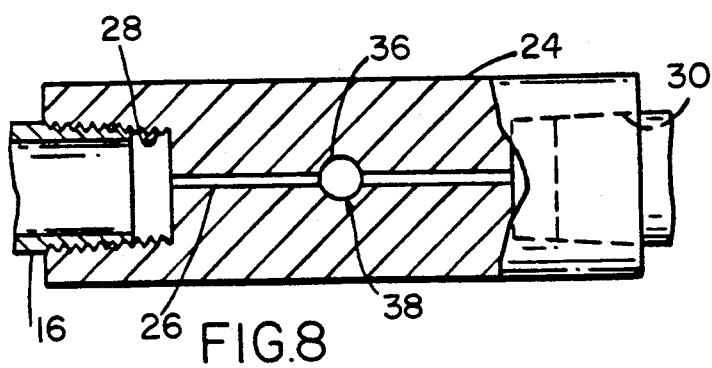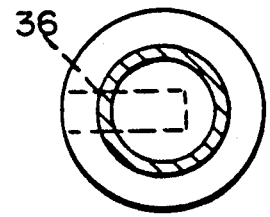

SAMPLING VALVE

This application is a continuation-in-part of U.S. application Ser. No. 312,471, filed Feb. 21, 1989, now abandoned.

BACKGROUND OF THE INVENTION

This invention relates to sampling valves and more particularly to a valve means and associated sample stream passageway that permits the safe sampling of process fluids through a conduit of a process stream under hazardous conditions while maintaining a fresh sample of the process fluids stream flowing through elements associated with the valve.

In process streams associated with fluid processes there is frequently a need for obtaining periodic samples of the process stream to provide the process operators with information for monitoring the productivity or progress of the process. In many such processes the process stream flowing through a conduit of the process is flowing under conditions that could be hazardous to personnel taking the sample; such hazards include high (or low) pressure, high temperature, extremely flammable or explosive streams, highly toxic streams, highly noxious streams, and many other possibly hazardous conditions. The taking of fluid samples of such process streams cannot usually be eliminated because of fear of the hazardous condition of the process stream, however the safety of the personnel taking the fluid sample should be of upmost concern to the process operators.

It is further a need that a fluid sample taken from a conduit of a process stream be truly representative of the condition of the process stream at the time that the fluid sample is taken. For that purpose, the taking of samples should be from a conduit of the process stream or a portion of the stream that is continuously in the process stream and therefore representative of the condition of the process stream at the time that the sample is taken. In some process stream sampling procedures, a sample is drawn from a portion of the process stream in a "one-way" sampling path. That is, the sample is drawn through some form of tubing not a conduit of the process stream and that sample is taken directly into the sample container. Some such sampling procedures require that a "flushing" portion of the sample pass through the "one-way" path to get to a "clean" sample of the stream. Such sampling procedures expose the sample taker to the hazardous conditions of the process which could include the high pressure or high velocity of the stream as the larger sample is wasted to get to the "clean" sample.

In other conventional sampling procedures or devices where there is not a continuous flow of the process stream in the sample passageway there may be a "dead" or "stale" volume of the process stream remaining in the passageways to the sampling device left from previous sampling procedures. That volume must be flushed or purged from the sampling device before the desired sample is taken if the sample is to be truly representative of the process conditions at the time of sample taking. While it may be the safest condition to stop the flow of the process stream during a sampling procedure, such an extreme condition would upset the process and cause productivity failures.

To avoid the foregoing, it is desirable that the taking of samples of a process stream be done with a sampling device that will eliminate or substantially reduce the exposure of the sample taker to any hazardous conditions, that will produce a sample that is truly representative of the process stream at the time that the sample is taken, and which sample taking will not interfere with the operation of a continuing process.

SUMMARY OF THE INVENTION

The object of the present invention is to provide a sampling valve and associated elements that will overcome the foregoing adverse conditions and will provide a sampling device that will permit the taking of clean, fresh samples of a process stream with no exposure of the sample taker to hazardous conditions associated with the process stream while at the same time not interrupting the continuation of the process being sampled.

That object is achieved by providing a valving mechanism attached to a conduit of a process stream in a manner to cause a portion of the process stream to flow through an element of the valving mechanism that will be effective in passing a portion of a process stream under conditions that will permit the sampling of the process stream under manageable pressure and flow so that the sample passing through the valve mechanism and to a sample container will avoid possibilities of exposure of the sample taker to the process stream.

A further object of the present invention, in accord with the preceding object, is to provide a Tee-body adapted to be connected to a conduit of a process stream across a differential pressure producer in a manner to provide a continuous flow of a portion of the process stream through the Tee-body and with further adaptations for the mounting of a suitable sampling valve to the Tee-body so as to permit the taking a representative sample of the process stream flow through the Tee-body.

A further object of the present invention, in accord with the preceding objects, is the provision of a Tee-body adapted for the close coupling of a sampling valve to the Tee-body; the Tee-body includes internal passageways and orifices for controlling the volume and pressure of the portion of a process stream passing through the Tee-body where the sampling valve is coupled.

A further object of the present invention, in accord with the preceding objects, is the provision of a Tee-body for use with a sampling valve wherein the Tee-body is adapted to pass a portion of a process stream and may include replaceable internal elements for the easy adaptation and adjustment of the Tee-body to different process stream conditions.

Another object of the present invention, in accord with the preceding objects, is the provision of an exit port, using the principles of fluidics, from the valve element of the present invention that will substantially eliminate the retention of any portion of the sampled stream at the exit port.

These and other objects of the present invention will be readily apparent to those skilled in the art from the appended drawings and specification illustrating preferred embodiments wherein:

BRIEF DESCRIPTION OF THE DRAWINGS

FIG. 1 is a front elevational view of the valve and Tee-body of the present invention.

FIG. 2 is a side elevational view of FIG. 1.

FIG. 4 is a partial sectional view of one form of the Tee-body of the present invention.

FIG. 5 is a side view of the Tee-body of FIG. 4.

FIG. 6 is a partial sectional view of another form of the Tee-body of the present invention.

FIG. 7 is a side view of the Tee-body of FIG. 6.

FIG. 8 is a partial sectional view of yet another form of the Tee-body of the present invention.

FIG. 9 is a side view of the Tee-body of FIG. 8.

COMPLETE DESCRIPTION OF THE INVENTION

Figures 12, 13:
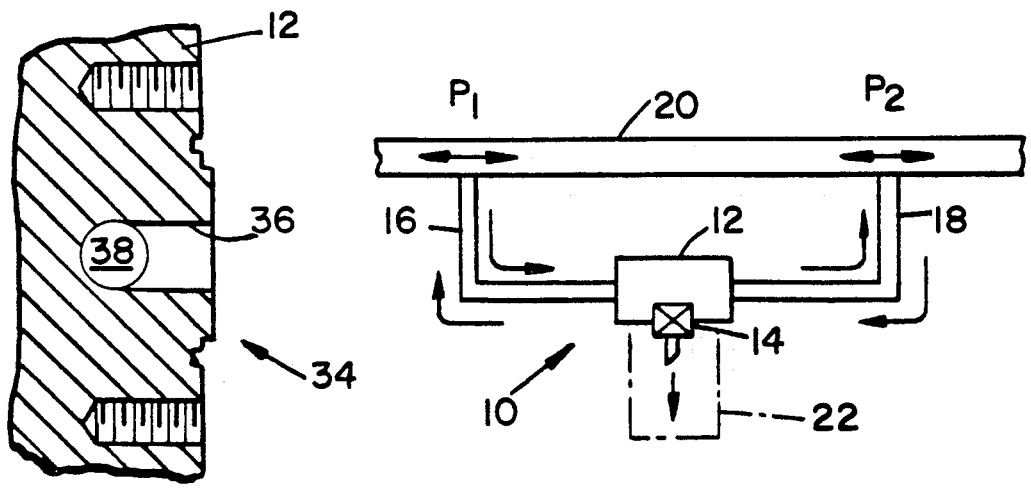
FIG. 12 is a sectional view through the Tee-body of FIGS. 4, 6 or 8 illustrating the mounting face for a valve device.
FIG. 13 is a schematic illustration of the installation of the sampling valve of the present invention in a process stream.

The sampling valve of the present invention is illustrated schematically in FIG. 13 as an assembly 10 comprising a Tee-body portion 12 and a valve element 14. The Tee-body portion 12 is connected by two conduits, 16 and 18, to a conduit 20 of a process flow stream or the like. It should be understood that there is a differential pressure between the input and output conduits as represented by the symbols $P_1$ and $P_2$. The flow of the process may be either from right-to-left or left-to-right of FIG. 13 for functional purposes of the sampling valve of the present invention. A sample container 22 is shown in phantom below the valve 14.

Figure 3:
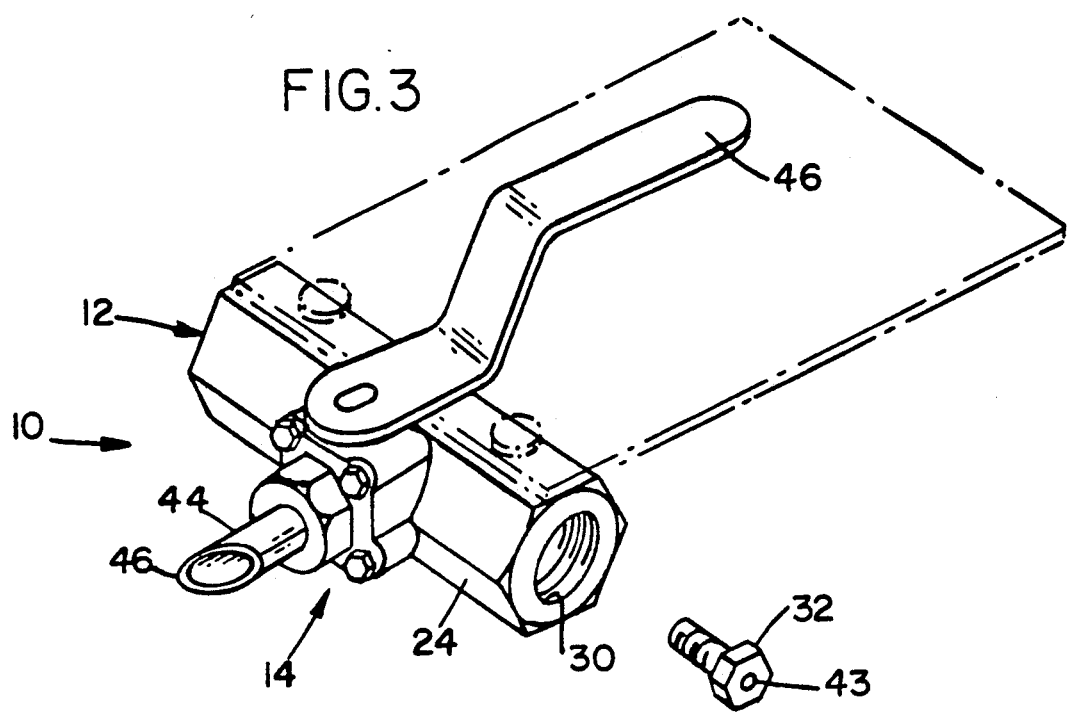
FIG. 3 is perspective view of the assembly of the present invention.

In FIGS. 1, 2 and 3 the sampling valve 10 is shown in elevation, side view and perspective illustrating the Tee-body 14 as a section of hexagonal body element 24 with an axial passageway 26 extending entirely through the body element 24 and terminating at openings at each end 28 and 30 thereof. In a preferred form of the body element 24, the end openings are adapted to be connected by conventional means to conduits (16 and 18) from a process stream with the connection being by choice either threaded or fixed. It will be seen that conventional pipe threading is a preferred connection manner to permit the internals of the Tee-body portion to be changed for use in different sampling operations. The end openings 28 and 30 extend only partially through the body portion 24 and, at their interior endings, the axial passageway 26 extends the remainder of the way between the two end openings.

The axial passageway 26 is of a smaller lateral dimension than the end openings and, for manufacturing convenience, is centered on the axis of the body element 24 and is preferrable round. At least the ends of the axial passageway adjacent to the inner ends of the end openings are threaded with pipe threads or machine threads to adapt them to be fitted with interior inserts 32 at either or both ends thereof. The function of the inserts 32 will be more fully defined hereinafter.

One exterior side of the body element 24 is machined and faced at 34 to prepare it to receive a face of the valve element 14. The mounting of the valve element 14 to the body element 24 must be secure and pressure tight to prevent any leaking between the two elements. At the faced surface 34 a lateral opening 36 is formed in the body element between the faced surface and the axial passageway 26 providing an unobstructed gallery area 38 at the intersection of the opening and the passageway. The mounting of the valve element at the machined and faced surface 34 is adapted to closely couple the valve element to the unobstructed gallery area and the lateral opening 36 at the interior of the Tee-body elements.

FIGS. 8 and 9 illustrate the simplest form of the body element 24, the axial passageway 26, the end openings 28 and 30, the lateral opening 36, and the gallery area 38. As there illustrated, the axial passageway 26 is an axial hole extending through the entire body element. The hole is preferrably circular in cross-section with a predetermined diameter established by the flow parameters desired in the sampling stream. In operation, the Tee-body portion would be connected by being threaded onto conduits 16 and 18 from the process stream as shown in FIG. 13, and a portion of the process stream would be directed into the body element and restricted by the reduced diameter axial passageway 26 through the body element. At the gallery area 38 where the axial passageway 26 and the lateral opening 36 intersect, the flow through the Tee-body becomes turbulent as the flow enters the gallery area and then proceeds through the Tee-body to exit at the opening 30. The turbulant flow is known in this art as creating a condition of VENA CONTRACTA. The turbulance within the gallery area 38 causes the sample stream to completely flush the interior of the gallery and to reduce the flow rate and pressure within the gallery. By properly proportioning the size of the axial passageway 26 to the size of the lateral opening 36 taking into consideration the type of process stream being sampled and the flow rate and pressure of that stream, the invention does prepare a condition for the sample stream within the gallery area 38 that will permit ease of sampling of the stream and a safe exit pressure and flow rate at the exit of the valve connected to the Tee-body.

Figure 10:
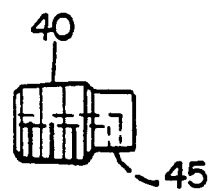
FIGS. 10 and 11 are elevational views of the inserts of FIGS. 4 and 6, respectively.
Figure 11:
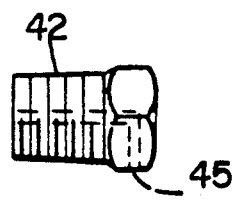

Alternative forms of the Tee-body are illustrated in FIGS. 4 and 6 where the axial opening 26 is larger than the fixed orifice opening of FIG. 8 and is preferrably threaded with machine or pipe threads to accomodate inserts 32 whose orifices are adapted to control the flow of the sample stream through the Tee-body. As illustrated in FIG. 4, the ends of the axial passageway 26 adjacent to the inner ends of the end openings 28 and 30 are threaded with standard pipe or machine threads so as to adapt the passageway 26 for the placement of an insert 32 at one or both ends. The insert 32 are not part of the connection of the Tee-body to the conduits 16 or 18 and may be in the form of a plug 40 as shown in FIG. 10 or in the form of a bolt head plug 42 as shown in FIG. 11. The inserts may be at one or both ends of the Tee-body 12. The insert 32 will be preformed with a restricting orifice through it either as an axial hole 43 or as a passageway formed as an elbow 45 partially axial through the body portion and partially lateral through the head or body portion. As illustrated in FIGS. 10 and 11, the elbow form provides for fluids to pass into and through the inserts and then into the interior of the body element 24 and the gallery area 38. The elbow path provides for additional control of the sample stream and reduces the velocity of the stream through the Tee-body, by an additional velocity head.

FIG. 3 illustrates an alternative form for the insert 32 there shown as a machine bolt with an axial hole 43. This form of Tee-body and insert is also illustrated in FIG. 6 where the axial passageway 26 is threaded with machine threads to be adapted to accomodate a machine bolt insert 32 of the type shown in FIG. 3.

FIG. 3 further illustrates the mounting of a valve element 14 to establish a close coupling of the valve element to the Tee-body 12. In the form shown, the valve element 14 is preferably a conventional ball valve with a handle 46 adapted to operate the internal ball of the valve. In a ball valve, the interior valving elements generally require a 90° turn to open the valve. Such a valve is adapted to be used with the present invention because the valve provides a complete open/closed position for the valve and the valve operating handle can be easily operated by a remote operating device (not shown). In a hazardous condition sampling operation, for which the sampling valve of the present invention is particularly useful, the remote operation of the valve after a sample container has been placed in receiving position would further protect personnel involved in the sample taking.

FIG. 12 is a sectional view through the Tee-body 12 illustrating the machined face 34 of the body element 24, the lateral hole 36, the gallery area 38, and threaded mounting holes for mounting a valve element to the Tee-body. It should be noted that the machined face is adapted to accomodate gaskets or sealing rings to insure that the valve and Tee-body interface is leak proof.

FIGS. 1, 2 and 3 illustrate an exit conduit means or sample draw tube 44 that is designed to substantially eliminate any retained drips of the sample volume on the exit conduit. The exit conduit means 44 is closely coupled to the exit port of the valve 14 so that little, if any, sampled fluids of the process stream are retained in the conduit 44 or in the elements of the valve 14. In the form shown, the end of the draw tube 44 is cut at a substantial angle, between 40° and 50° and preferably at 45°, so that any sample passing through the conduit and clinging to the interior walls of the conduit by capillary attraction will encounter an end of the conduit that is not symetrical. Such an end to the conduit breaks the capillary cling forces and causes the film on the interior of the conduit to flow toward the lowest end of the conduit. In the case shown here, the conduit will form a final flow from the tip 46 where there is a minimal chance that a drip will be retained by the conduit. This advantage is of particular importance in the sampling of toxic fluid streams that might present an unwanted hazard to those taking the samples or to the environment.

The sampling valve herein described is composed of a minimum of parts and provides a means for sampling a clean portion of a process stream in a manner that will not hinder or harm the process it is sampling. The sampling valve treats the sample stream in a manner to reduce the velocity and turbulance of the flow of the stream to permit the sample to be taken from a manageable stream. The taken sample is conveyed to a sample container through a conduit that substantially eliminates the retention of any portion of the sample. The functional portions of the sampling valve are easily connected to a sample stream and are easily modified to adapt the sampling valve to different process stream conditions. The apparatus may also be adapted to sample process streams that are under pressure or vacuum, cold or hot, and of varying viscosities.

It should be understood that the restricting of the sample stream flow through a narrowed passageway within the Tee-body and/or through interior inserts with restricted flow paths causes progressive reductions in the pressure of the stream through the Tee-body. The lateral opening intersecting the axial passageway creates an internal gallery area and, with the axial opening being at least as large and preferably larger in diameter than the restricting orifice, the gallery area is less restrictive than the passageway to it. The eventual opening of the restricted flow into the internal gallery causes a desired turbulance of sample flow that conditions the sample stream within the gallery area to a manageable flow rate and pressure. When so conditioned, the taking of a sample through a suitable valve produces a sample at the exit conduit of the valve that will be non-turbulant and at acceptable volume and pressure. The taking of the sample in that manner substantially eliminates spurting of the sample into a container, such spurting could cause splashing on the sample taker, and substantially eliminates hazard to the sample taker or the surrounding environment.

While certain preferred embodiments of the invention have been specifically disclosed, it should be understood that the invention is not limited thereto as many variations will be readily apparent to those skilled in the art and the invention is to be given it broadest possible interpertation within the terms of the following claims.

I claim:

1. A Tee-body for use in a system for sampling process fluids flowing through a conduit of a process stream, wherein a continuously fresh sample of said process fluids within said Tee-body is desired and wherein said Tee-body is attachable to said conduit of said process stream between portions of said conduit wherein a pressure differential exists so as to cause continuous flow of a portion of said process fluids through said Tee-body, said Tee-body including a closely coupled sample exit conduit means and a valving system attached to and forming a part of said Tee-body, said Tee-body comprising:

(a) a body element having areas definable as two end areas and a central gallery area between said end areas, (b) a restrictive axial passageway of predeterminable size through said body element between said end areas establishing flow controlling restricting orifices at each of said two end areas with said axial passageway opening into and exiting from said central gallery area, (c) means at each of said two end areas of said body element for attaching said body element to a portion of said conduit of said process stream between said portions of said conduit where said pressure differential exists whereby a portion of said process fluids within said conduit flows continuously through said restrictive axial passageway into said central gallery area and out of said central gallery area through said body element, (d) a lateral opening from the exterior of said body element extending at least partially through said body element between said two end areas and extending into said central gallery area so as to closely couple said exterior and said central gallery area, said lateral opening having a size in cross-sectional dimensions at least as large as the size in cross-sectional dimension of said axial passageway to form an unobstructed open volume portion of said central gallery area within said Tee-body, the intersection of said lateral opening and said axial passageway defining said unobstructed open volume portion at said central gallery area within said body element, said unobstructed open volume portion and said lateral opening at said central gallery area adapted to be flushed by said process fluid flow through said predetermined controlled axial passageway of said Tee-body to establish continuously vena contracta turbulant process fluid flow within and a fresh sample of said process fluids within said unobstructed open volume portion of said central gallery area and said lateral opening, said predetermined size of said restrictive axial passageway and the size of said lateral opening being proportioned to cause said vena contracta turbulant flushing, fluid flow so as to produce said fresh process fluid sample within said unobstructed open volume portion of said central gallery area and said lateral opening at a manageable pressure and flow rate, (e) a valve means including means for attaching said valve means to said exterior of said body element at said lateral opening, (f) and an exit conduit means, (g) said valve means being positioned between and closely coupled to said gallery area and said exit conduit means from said Tee-body at said lateral opening and at said exterior of said body element whereby said valve means may control passage of said fresh process fluid sample between said flushed central gallery area and said exit conduit means through said flushed lateral opening.

2. The Tee-body of claim 1 wherein said restrictive axial passageway through said body element terminates at said two end areas in threaded openings adapted to be connected to an input and an output portion along said conduit in said process stream.

3. The Tee-body of claim 1 wherein said restrictive axial passageway through said body element is of a first diameter through said central gallery area of said body element, a pair of inserts in said axial passageway between said means for attaching said body element to said conduit of said process stream and said central gallery area, one of said pair of inserts at each end of said axial passageway, said inserts extending only partially through said axial passageway within said body element so as to define axial portions of said central gallery area along said axial passageway, each of said inserts having an axial hole therethrough, said axial hole through said inserts being smaller than said first diameter axial passageway through said body element and being of a predetermined size to define said orifices and to control passage of said portion of said fluids within said conduit passing through said body element.

4. The Tee-body of claim 3 wherein said restrictive axial passageway through said body element is adapted to be controlled in a predetermined manner by controlling the size of said axial hole through said inserts.

5. The Tee-body of claim 3 wherein said axial passageway of said first diameter is threaded and said pair of inserts are threaded with threads corresponding to said threads through said axial passageway, said inserts being adapted to be threaded into said axial passageway without connecting to said means for attaching said body portion to said conduit of said process stream.

6. The Tee-body of claim 1 wherein said axial passageway and said lateral opening have circular cross-sections, and said lateral opening has a diameter at least as large as the diameter of said axial passageway.

7. The Tee-body of claim 6 wherein said lateral opening has a diameter larger than the diameter of said axial passageway to establish said unobstructed open volume portion of said central gallery area with said Tee-body.

8. The Tee-body of claim 1 wherein said unobstructed central gallery area affects a reduced velocity and increased nonuniform vena contracta flow turbulance of said fluid flow for said portion of said fluid within said conduit flowing within said unobstructed central gallery area and said lateral opening, said lateral opening providing access to said affected portion of said fluid flowing in said unobstructed central gallery area and said lateral opening to said valve means.

9. The Tee-body of claim 1 wherein said exit conduit means terminates in an opening having a diagonal angle cut across said exit conduit means for the purpose of reducing surface tension in fluid samples passing through said opening in said conduit means.

10. The Tee-body of claim 9 wherein said diagonal angle cut across said exit conduit means is 45° with respect to an axial dimension of said exit conduit means.

11. The Tee-body of claim 1 with an external control lever attached to said valve means for opening and closing said valve means to permit passage between said gallery and said exterior of said body element through said valve means.

12. The Tee-body of claim 11 wherein said body element, axial passageway, unobstructed central gallery area, lateral opening, valve means and exit conduit means are so constructed and arranged as to permit continuous flow of said portion of said fluids within said conduit of said process stream through said body element to maintain a fresh sample portion of said process stream passing through said body element, with said fresh sample portion of said process stream being controlled in turbulance and pressure by said restrictive axial passageway to maintain a clean central gallery area and lateral opening by said vena contracta turbulance, and said fresh sample portion being a controlled passage at desirable pressure, said controlled passage between said central gallery area and said lateral opening to said exterior of said body element through said valve means provides said fresh sample portion of said process stream at controllable safe volume and desirable pressure, and said exit conduit means dispenses the entirety of said fresh sample without retaining a drip thereof.

* * * * *